United States Patent [19]

Nagatsuka et al.

[11] Patent Number: 4,988,872

[45] Date of Patent: Jan. 29, 1991

[54] ELECTRON PROBE MICROANALYZER HAVING WAVELENGTH-DISPERSIVE X-RAY SPECTROMETER AND ENERGY-DISPERSIVE X-RAY SPECTROMETER

[75] Inventors: Yoshitaka Nagatsuka; Masayuki Ohtsuki; Masaki Saito; Koji Yoshida; Kazuyasu Kawabe, all of Tokyo, Japan

[73] Assignee: JEOL Ltd., Tokyo, Japan

[21] Appl. No.: 386,416

[22] Filed: Jul. 27, 1989

[30] Foreign Application Priority Data

Jul. 28, 1988 [JP] Japan ............................ 63-189193

[51] Int. Cl.$^5$ .......................................... G01N 23/04
[52] U.S. Cl. ............................... 250/310; 250/306; 250/397; 378/45; 378/46; 378/53; 378/88
[58] Field of Search ............... 250/310, 307, 306, 397; 378/45, 46, 83, 88

[56] References Cited

U.S. PATENT DOCUMENTS

| | | | |
|---|---|---|---|
| 3,204,095 | 8/1965 | Watanabe | 250/310 |
| 3,235,727 | 2/1966 | Shapiro | 250/310 |
| 3,333,100 | 7/1967 | Cilyo | 250/310 |
| 3,514,599 | 5/1970 | Campbell | 250/310 |
| 3,694,635 | 9/1972 | Hoetzel et al. | 250/310 |
| 3,914,605 | 10/1975 | Hara | 250/276 |
| 3,942,005 | 3/1976 | Watanabe | 250/310 |
| 4,219,731 | 8/1980 | Migitaka et al. | 250/310 |
| 4,253,154 | 2/1981 | Russ et al. | 364/527 |
| 4,288,692 | 9/1981 | Schamber et al. | 250/310 |
| 4,331,872 | 5/1982 | Saga et al. | 250/310 |
| 4,426,577 | 1/1984 | Koite et al. | 250/310 |
| 4,724,320 | 2/1988 | Ino et al. | 250/307 |
| 4,777,364 | 10/1988 | Sartore | 250/310 |
| 4,857,731 | 8/1989 | Tagata | 250/310 |
| 4,885,465 | 12/1989 | Nagasuka et al. | 250/310 |

OTHER PUBLICATIONS

"X-Ray Fluorescence Analysis", *McGraw-Hill Encyclopedia of Science and Technology*, vol. 14, pp. 658–662.
"Electron Probe Microanalysis in Health Research", *McGraw-Hill Yearbook of Science and Technology* 1979 Review 1980 Review, Richard J. Roman, Claude Lechene, pp. 53–61.

*Primary Examiner*—Jack I. Berman
*Assistant Examiner*—Kiet T. Nguyen
*Attorney, Agent, or Firm*—Webb, Burden, Ziesenheim & Webb

[57] ABSTRACT

An electron probe microanalyzer equipped with a wavelength-dispersive x-ray spectrometer and also with an energy-dispersive x-ray spectrometer. X-rays emanating from the same sample region are detected by these two spectrometers, and spectra are created from the detected x-rays. Cursors which can be moved at will are superimposed on the spectra. One of the cursors is moved in relation to the other. That is, when one cursor is moved into the position of a desired wavelength or energy, the other is moved into the position of the corresponding energy or wavelength. The use of the cursors enables one to precisely and easily find the existence of a certain element in the sample region from the spectra obtained by the two x-ray spectrometers.

6 Claims, 3 Drawing Sheets

ELECTRON PROBE MICROANALYZER HAVING WAVELENGTH-DISPERSIVE X-RAY SPECTROMETER AND ENERGY-DISPERSIVE X-RAY SPECTROMETER

FIELD OF THE INVENTION

The present invention relates to an electron probe microanalyzer equipped with a wavelength-dispersive x-ray spectrometer and also with an energy-dispersive x-ray spectrometer.

BACKGROUND OF THE INVENTION

An electron probe microanalyzer equipped with a wavelength-dispersive spectrometer is disclosed, for example, in U.S. Pat. No. 3,914,605. Electron probe microanalyzers equipped with an energy-dispersive x-ray spectrometer are disclosed, for example, in U.S. Pat. Nos. 4,253,154, No. 4,697,080, and No. 4,724,320. In these electron probe microanalyzers, an electron beam is caused to impinge on the surface of a specimen. The characteristic x-rays emanating from the specimen are detected by a wavelength-dispersive or energy-dispersive x-ray spectrometer, and an x-ray spectrum is displayed according to the result of the detection. Thus, the elements included in the specimen are identified according to the spectrum.

The wavelength-dispersive spectrometer and the energy-dispersive spectrometer have different features. In particular, the wavelength-dispersive x-ray spectrometer exhibits high resolution in terms of wavelengths, but it cannot easily remove higher-order x-rays it entails. On the other hand, the spectrum obtained by the energydispersive spectrometer has no higher-order x-rays, but shows poor energy resolution. Especially, it cannot easily detect quite light elements, for example, in the range from beryllium to fluorine.

Accordingly, it is the common practice to detect x-rays with only a wavelength-dispersive x-ray spectrometer (WDS) or an energy-dispersive x-ray spectrometer (EDS). The obtained WDS or EDS spectrum is displayed on a display device to identify elements. When elements are identified based on only a WDS spectrum, the operator might misidentify the included elements because of higher-order x-rays. On the other hand, when elements are identified based on only an EDS spectrum, peaks tend to overlap due to poor energy resolution. As a result, the operator might overlook some elements included.

In view of these problems, the present inventors have already proposed an electron probe microanalyzer equipped with a wavelength-dispersive x-ray spectrometer and also with an energy-dispersive x-ray spectrometer in U.S. patent application Ser. No. 215,222 entitled "Spectrum Display Device For X-Ray Microanalyzer Or The Like". In this proposed microanalyzer, two kinds of spectra are displayed, based on the x-rays obtained from the same specimen region under investigation by the two kinds of spectrometers. An element-designating means is provided to permit one to designate any desired chemical element. Further, there is provided a means which superimposes markers or cursors on the displayed spectra to indicate the energies or wavelengths of the characteristic x-rays emanating from the element designated by the element-designating means. The present invention pertains to improvements over this proposed microanalyzer.

SUMMARY OF THE INVENTION

It is a main object of the present invention to provide an electron probe microanalyzer which superimposes interrelated markers or cursors on two kinds of x-ray spectra obtained by the use of a wavelength-dispersive x-ray spectrometer and an energy-dispersive x-ray spectrometer, to make qualitative analysis with improved accuracy.

It is another object of the invention to provide an electron probe microanalyzer in which interrelated markers display the names of chemical elements that are likely to produce characteristic x-rays, at the positions designated by the markers, whereby making qualitative analysis with improved accuracy.

Briefly, according to this invention, an electron probe microanalyzer has a wavelength-dispersive x-ray spectrometer and an energy-dispersive x-ray spectrometer, and spectra obtained from the same specimen region by the two spectrometers are displayed. Cursors which can be moved at will are superimposed on the spectra. One cursor moves in relation to the other. If one of the two cursors is brought into the position of a desired wavelength or energy, the other moves into the position of the corresponding energy or wavelength.

DESCRIPTION OF THE PREFERRED EMBODIMENT

Figure 1:
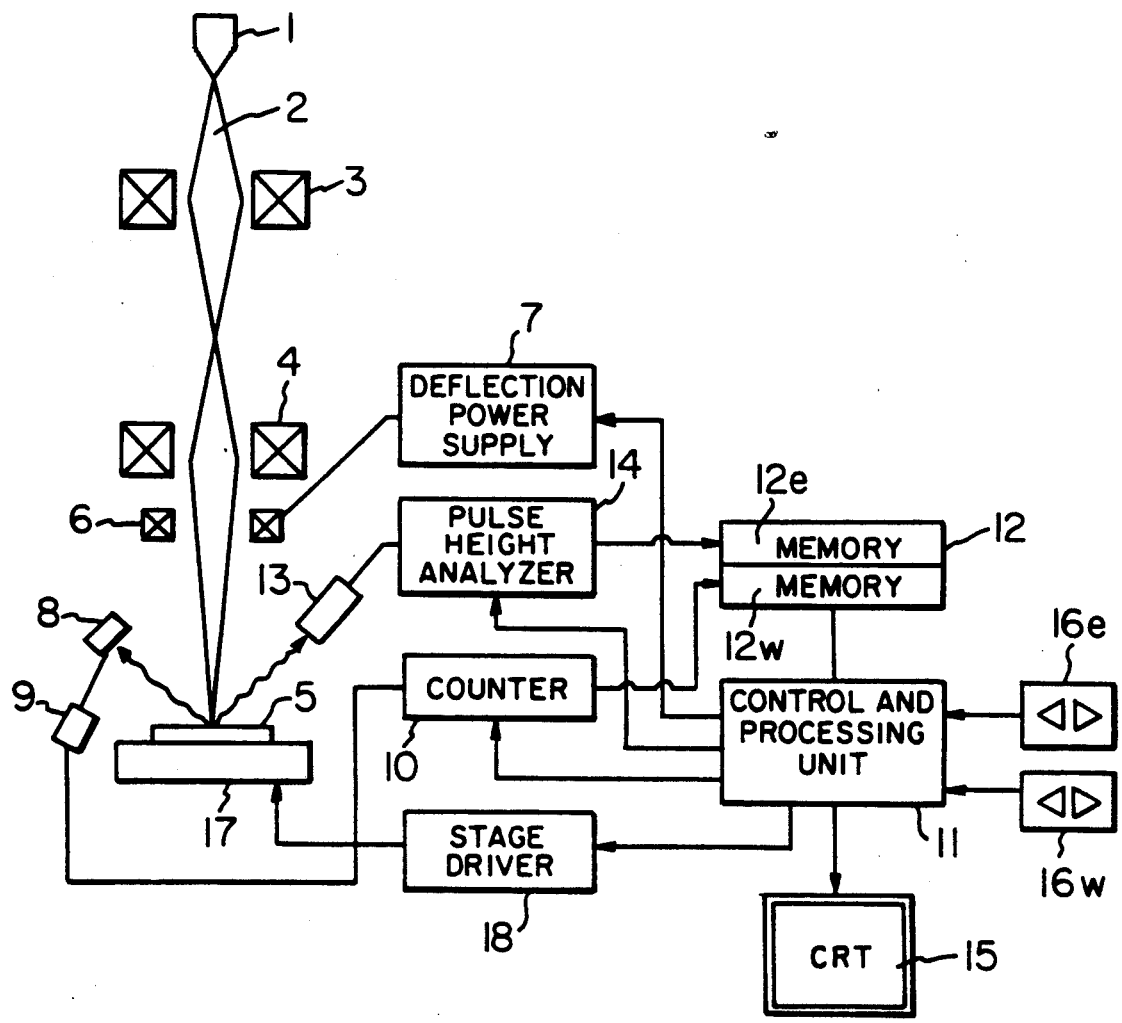
FIG. 1 is a block diagram of an electron probe microanalyzer according to the invention.

Referring to FIG. 1, there is shown an electron probe microanalyzer according to the invention. This instrument includes an electron gun 1 producing an electron beam 2, a condenser lens 3, and a final-stage focusing lens 4. The beam 2 is focused sharply by the lenses 3 and 4 and directed onto a specimen 5. An electron beam-scanning coil 6 is disposed either to permit the operator to arbitrarily select the position on the specimen 5 that is irradiated with the beam 2 or to make the beam 2 scan the specimen surface in two dimensions. A deflection power supply 7 supplies a deflection current to the scanning coil 6.

Disposed above the specimen 5 are a spectral crystal 8, an x-ray detector 9, and a semiconductor x-ray detector 13. The crystal 8 and the detector 9 together form a wave-dispersive x-ray spectrometer (WDS). The detector 13 forms an energy-dispersive x-ray spectrometer (EDS). X-rays emanating from the specimen 5 and arriving at the spectral crystal 8 are dispersed by the crystal 8. Only a certain wavelength of the x-rays is directed onto the x-ray detector 9. The spectral crystal 8 and the x-ray detector 9 are moved such that a given relationship between them is maintained. Thus, different wavelengths of x-rays impinge on the detector 9 successively. As a result, the specimen is wavelength swept. The present instrument includes additional spectral crystals (not shown) similar to the spectral crystal 8. These crystals are selectively used. The output pulses from the x-ray detector 9 are amplified by an amplifier (not shown) and then fed to a counter circuit 10, which counts its incoming pulses for a time set by a control signal produced from a control unit 11. The total count which is obtained by the counter circuit 10 and represents a wavelength spectrum derived by the wavelength-dispersive x-ray spectrometer (WDS) is stored in a memory 12w for the WDS.

When x-rays emanating from the specimen 5 impinge on the semiconductor detector 13 forming the energy dispersive x-ray spectrometer (EDS), it produces a pulse signal having a pulse height corresponding to the energy of the incident x-rays. The pulse signal is sent via an amplifier (not shown) to a multi-channel pulse-height analyzer 14 which converts its input pulses into an energy spectrum. Data about the resulting spectrum is sent to a memory 12e for the EDS and stored in this memory.

A cathode-ray tube 15, cursor shifters 16w, 16e are connected with the control unit 11. X-ray spectra are displayed on the CRT 15. The control unit 11 supplies a control signal to a stage driver 18 which moves a specimen stage 17 in two or three dimensions. The specimen 5 is carried on the specimen stage 17.

In the above-described structure, the x-rays produced from the specimen 5 by the irradiation of the electron beam 2 are detected by the wavelength-dispersive x-ray spectrometer and the energy-dispersive x-ray spectrometer. The wavelength transmitted by the wavelength-dispersive spectrometer is swept from a short wavelength to a long wavelength, or vice versa. At the same time, data obtained by the counter 10 are successively stored in the memory 12w at successive addresses. In this way, data about the x-ray spectrum derived by the wavelength-dispersive spectrometer is collected.

In the energy-dispersive x-ray spectrometer, the x-rays emanating from the specimen 5 are detected by the semiconductor detector 13 to obtain pulse signals proportional to the enerqies of the x-rays. The multi-channel pulse-height analyzer 14 sorts the output pulses from the detector 13 into selected ranges of amplitude and counts the numbers of the pulses falling into their respective ranges. The counted numbers representing an energy spectrum are stored in the memory 12e at successive addresses under the control of the control unit 11.

Figure 2:
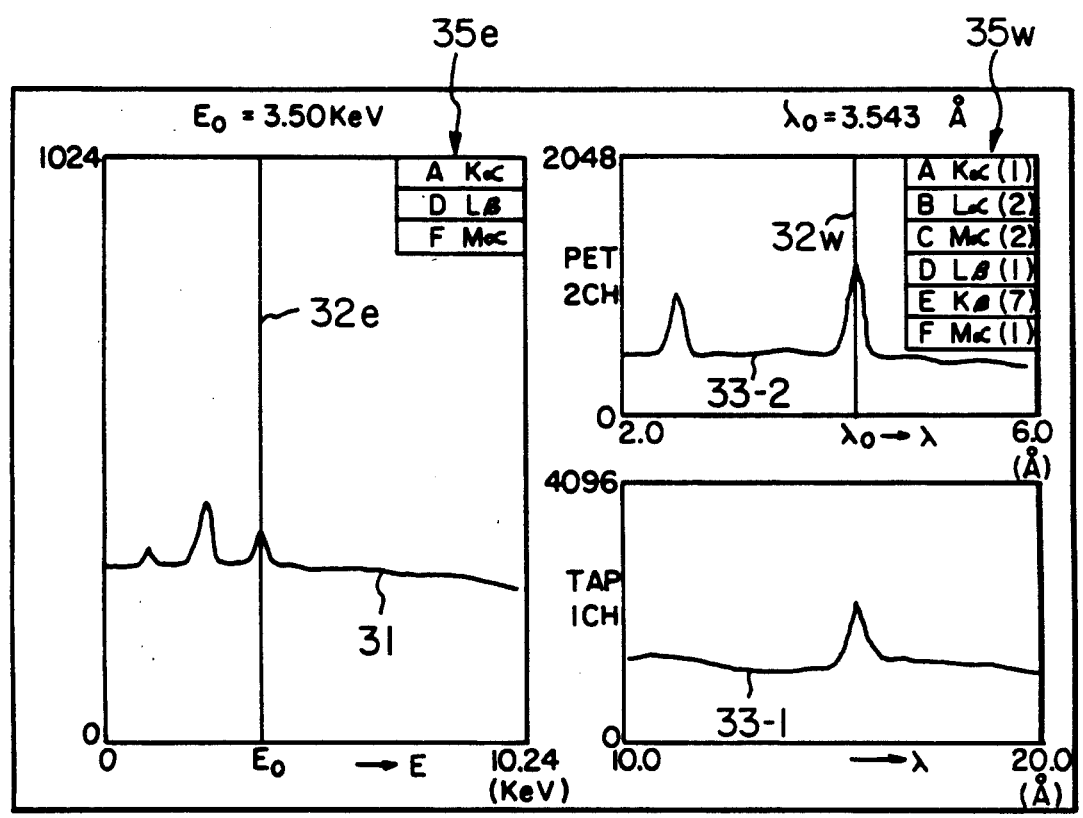
FIG. 2 is a diagram illustrating one example of the picture on the viewing screen of the display device shown in FIG. 1.

The control unit 11 presents WDS spectra 33 and an EDS spectrum 31 simultaneously on the screen of the cathode-ray tube 15 as shown in FIG. 2 according to the spectral data stored in the memories 12w and 12e, respectively. The WDS spectra 33 comprise two spectra 33-1 and 33-2 obtained by the use of a TAP crystal and a PET crystal, respectively, for two channels. As shown in FIG. 2, vertical cursors 32w and 32e are superimposed on the spectra, respectively. The operator can move the cursors 32w and 32e right and left by depressing direction-specifying buttons on the cursor shifters 16w and 16e.

The control unit 11 stores a table of kinds of characteristic x-rays produced by a number of elements, orders n, and wavelengths, λ, for the wavelength-dispersive spectrometer. Further, the control unit 11 stores a table of the names of a number of elements and the energies E of the characteristic x-rays produced by the elements, for the energy-dispersive spectrometer.

The present instrument can operate in any one of three modes, i.e., (1) WDS identification mode, (2) EDS identification mode, and (3) WDS-EDS linking mode, for qualitative analysis.

In the WDS identification mode, the operator operates the cursor shifter 16w to move the cursor 32w into the position of a desired peak when the operator desires to know what element gave rise to the peak on the WDS spectrum 33-2. The control unit calculates the wavelength $\lambda_o$ from the position of the cursor. This wavelength $\lambda_o$ is collated with the aforementioned table of the wavelengths and the elements. Then, a list 35w of the names of elements A–F which might produce the characteristic x-rays of the wavelength $\lambda_o$ and the kinds of characteristic x-rays (K$\alpha$, L$\alpha$, etc.). If the difference between a wavelength $\lambda$ selected by the collation and the wavelength $\lambda_o$ lies within a predetermined tolerable range, then the element corresponding to the wavelength $\lambda$ is regarded as a candidate for the correct element. This candidate element is included in the list 35w, together with the kinds of the characteristic x-rays.

The wavelength-dispersive spectrometer may detect higher-order diffraction x-rays. Therefore, the higher-order diffraction x-rays are also taken into account in collating the wavelength with the table as described above. In particular, a higher-order diffraction x-radiation having a wavelength nλ (the order n lies in a predetermined range) is selected by the collation. If the difference between the wavelength nλ and the calculated wavelength $\lambda_o$ lies within a predetermined range, then the element corresponding to the wavelength $\lambda$ is displayed as a candidate for the correct element, together with the kind of the characteristic x-rays and the order n. For this purpose, the following relations must be met:

$$\lambda_o - w \leq n\lambda \leq \lambda_o + w \quad (1)$$

where w is the allowed range of wavelengths, n is the order and given by n = 1, 2,..., N (N is the maximum value of the specified orders).

In the EDS identification mode, the operator operates the cursor shifter 16e to move the cursor 32e into the position of a desired peak, for knowing what element produced the peak on the EDS spectrum 31. The control unit 11 computes the energy $E_o$ from the position of the cursor. The energy $E_o$ is collated with the table of the energies and the elements. Then, a list 35e of the names of elements A–F which might produce the characteristic x-rays of the energy $E_o$ and the kinds of the characteristic x-rays K$\alpha$, L$\beta$, etc. is displayed. An energy E is selected by the collation. If the difference between the energy E and the energy $E_o$ lies within a predetermined range, then the element corresponding to the energy E is displayed in the list 35e as a candidate for the correct element, together with the kinds of the characteristic x-rays. For this purpose, the following condition must be satisfied:

$$E_o - u \leq E \leq E_o + u \quad (2)$$

where u is the allowed range of energies.

Figure 3:
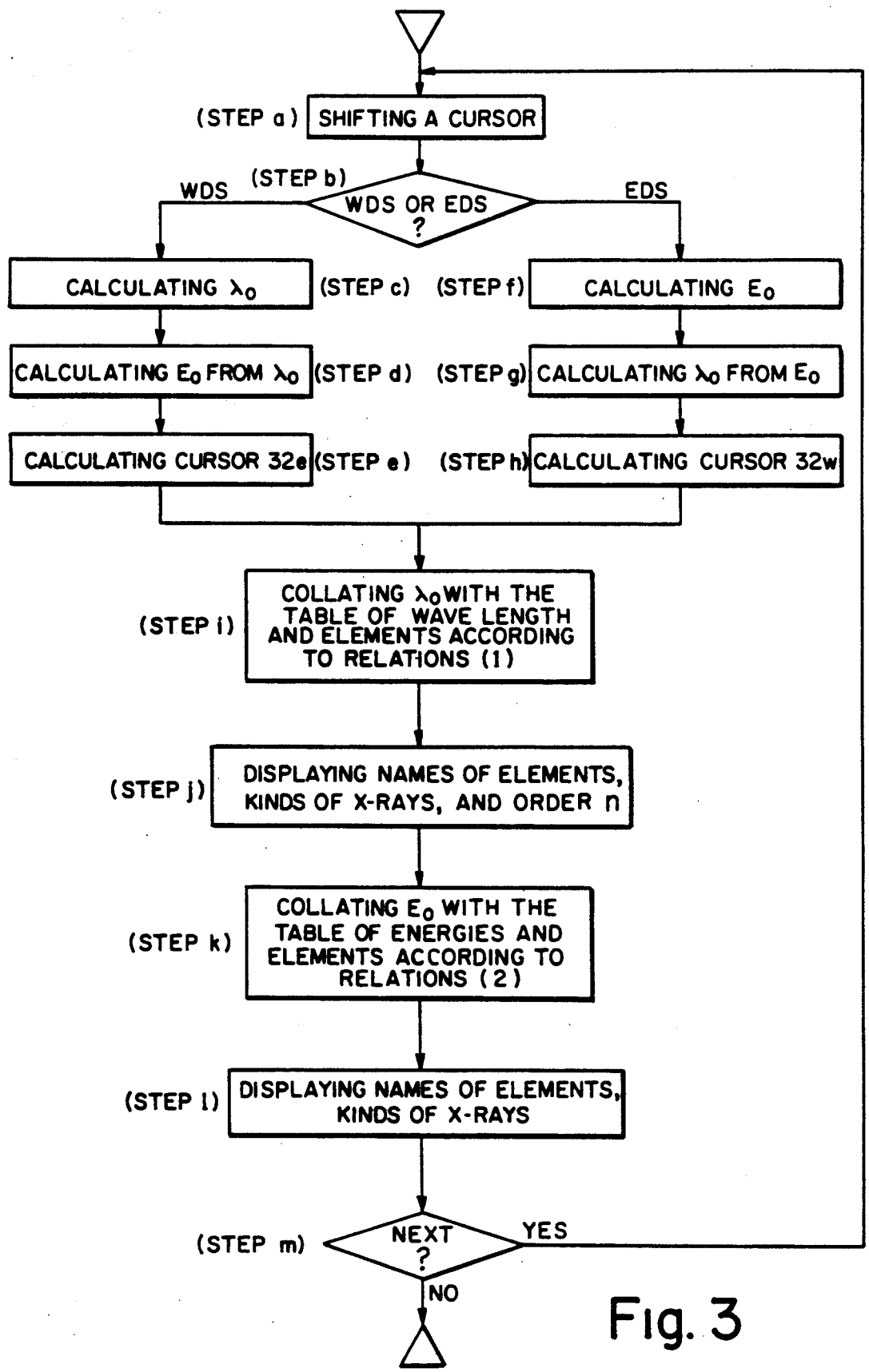
FIG. 3 is a flowchart illustrating a sequence of operations performed in the WDS-EDS linking mode.

In the WDS-EDS linking mode, a series of operations is performed for identification as illustrated in the flowchart of FIG. 3. First, the operator operates the cursor shifter 16w or 16e to move the cursor 32w or 32e into the position of a desired peak lying on a WDS or EDS spectrum (step a). Then, the control unit 11 ascertains whether the shifted cursor is the cursor 32w for the WDS or the cursor 32e for the EDS (step b). If the cursor moved by the operator is the cursor 32w for the WDS, the control unit 11 calculates the wavelength $\lambda_o$ from the position of the cursor (step c). Subsequently, the control unit 11 calculates the corresponding energy $E_o$ from the wavelength $\lambda_o$, utilizing the relation $$E = 12,398/\lambda \quad (3)$$

which exists between the wavelength λ (in angstrom) of the characteristic x-rays and the energy E (in eV) (step d). The control unit 11 moves the cursor 32e, which was on the EDS spectrum and was not shifted by the operator, into the position corresponding to the calculated energy $E_o$ (step e). If the cursor moved by the operator is the cursor 32e for the EDS, then the control unit 11 calculates the energy $E_o$ from the position of the cursor (step f). The control unit 11 computes the wavelength $\lambda_o$ from the calculated energy $E_o$ according to equation (3) described above (step g). The control unit 11 moves the cursor 32w, which was on the WDS spectrum and was not moved by the operator, into the position corresponding to the calculated wavelength $\lambda_o$ (step h).

By these steps a–h, one cursor is moved by the operator, while the other is moved into the corresponding position on the other spectrum in relation to the movement of said one cursor. As a result, the wavelength $\lambda_o$ or the energy $E_o$ have been calculated.

The control unit 11 collates the wavelength $\lambda_o$ with the table of the wavelengths and the elements. Then, it provides a display of the list 35w of the names of elements A–F that might produce the characteristic x-rays of the wavelength $\lambda_o$ and the kinds of the characteristic x-rays ($K\alpha$, $L\alpha$, etc.) and order n. The collation and the display are provided in exactly the same manner as in the WDS identification mode (steps i and j).

Thereafter, the control unit 11 collates the energy $E_o$ with the table of the energies and the elements, and it displays the list 35e of the names of the elements A–F which might produce the characteristic x-rays of the energy $E_o$ and the kinds of the characteristic x-rays ($K\alpha$, $L\alpha$, etc.). The collation and the display are provided in exactly the same manner as in the EDS identification mode (steps k and l). Thus, the series of identification operations is completed. If there is any additional operation, then control goes back to step a (step m).

In the aforementioned WDS-EDS linking mode, when the cursor on one of the WDS and EDS spectra displayed simultaneously is moved into a desired position, the cursor on the other spectrum is automatically moved into the corresponding position. Therefore, the operator can very easily see whether the two kinds of spectra contain peaks produced by a common element. Concurrently, collations are made, and the lists 35w and 35e indicating the results of the collations are shown at the same time. Comparing the two lists insures that the elements included in the specimen are identified with greater ease and more certainty.

While there has been described a preferred form of the invention, obviously modifications and variations are possible in light of the above teachings. For example, it is not always essential that the WDS and EDS spectra be obtained simultaneously by the same measurement. They may be derived by separate measurements made of the same specimen at different instants of time.

In the above example, the two cursor shifters 16w and 16e are provided, and either of them can be moved by the operator. It is also possible to provide only one shifter so that only one cursor may be moved by the operator. In this case, the step b for ascertaining which of the cursors is operated can be omitted. Also, it is not always necessary that wavelength be plotted on the horizontal axis of the wavelength spectrum obtained by the wavelength-dispersive spectrometer. What is plotted on the horizontal axis can also be the spectrometer position proportional to wavelength or converted energy values. In any case, the elements included in the specimen can be identified accurately.

In the above example, one energy spectrum and two wavelength spectra are displayed to identify the elements included in the specimen. The numbers of the displayed spectra are not restricted to these numbers. Also in the above example, an EDS spectrum is displayed on the left half of the viewing screen of the CRT 15, while WDS spectra are displayed on the right half at the same time. The invention is not limited to this method of display. For instance, the EDS spectrum is displayed on the upper half of the screen, while the WDS spectra are presented on the lower half at the same time. Both kinds of spectra may be simultaneously displayed on two separate cathode-ray tubes, respectively, which are disposed close to each other.

Having thus described our invention with the details and particularity required by the Patent Laws, what is claimed and desired protected by Letters Patent is set forth in the following claims.

What is claimed is:

1. An electron probe microanalyzer comprising:
   a means for irradiating the surface of a specimen with an electron beam;
   a wavelength-dispersive x-ray spectrometer and an energy-dispersive x-ray spectrometer which detect x-rays emanating from the specimen by the irradiation;
   display means on which first and second spectrum being two kinds of spectra created from the x-rays emitted from the same sample region under investigation and detected by the spectrometers are displayed;
   means for superimposing a first and a second cursor on the first and second spectrum respectively displayed on the display means to indicate the positions of the energies or wavelengths of characteristic xrays;
   a means for manually moving the position of the first cursor; and
   a means for automatically moving the second cursor in relation to the position indicated by the first cursor such that the energy indicated by one of the cursors corresponds to the wavelength indicated by the other.

2. The electron probe microanalyzer of claim 1, wherein said means for automatically moving the second cursor on the second spectrum in relation to the position indicated by the first cursor on the first spectrum comprises a conversion means that determines a position lying on the second spectrum corresponding to the position indicated by the first cursor on the first spectrum, and a means for bringing the second cursor into the position that is determined by the conversion means.

3. The electron probe microanalyzer of claim 1 or 2, further comprising a means for making an identification by reference to a stored table associating named elements and characteristic energies and wavelengths for emitted x-rays utilizing the wavelengths or energies corresponding to the positions indicated by the first and second cursors, and a means for displaying the result of the identification near the spectra.

4. An electron probe microanalyzer comprising:
   a means for irradiating the surface of a specimen with an electron beam;
   a wavelength-dispersive x-ray spectrometer and an energy-dispersive x-ray spectrometer which detect x-rays emanating from the specimen by the irradiation;

display means on which spectra created from the xrays emitted from the same sample region under investigation and detected by the spectrometers are displayed;

means for superimposing a first and a second cursor on the two kinds of spectra displayed on the display means to indicate the positions of energies or wavelengths of characteristic x-rays;

a means for moving the first cursor;

a means for moving the second cursor;

a means which ascertains which of the cursors has been moved; and a means which automatically moves the cursor that has not been moved, in relation to the position indicated by the cursor already moved such that the energy indicated by one of the cursors corresponds to the wavelength indicated by the other.

5. The electron probe microanalyzer of claim 4, wherein said means for moving the cursor that has not been moved, in relation to the position indicated by the cursor already moved comprises a conversion means that determines a position lying on one spectrum and corresponding to the position indicated by the cursor already moved, the last-mentioned cursor lying on the other spectrum; and a means for bringing the cursor that has not been moved into the position which is determined by the conversion means and lies on the other spectrum.

6. The electron probe microanalyzer of claim 4 or 5, further comprising a means for making an identification utilizing the wavelengths or energies corresponding to the positions indicated by the first and second cursors, respectively; and a means for displaying the result of the identification near the spectra.

* * * * *

UNITED STATES PATENT AND TRADEMARK OFFICE
CERTIFICATE OF CORRECTION

PATENT NO. : 4,988,872

DATED : January 29, 1991

INVENTOR(S) : Yoshitaka Nagatsuka, Masayuki Ohtsuki, Masaki Saito, Koji Yoshida and Kazuyasu Kawabe It is certified that error appears in the above-identified patent and that said Letters Patent is hereby corrected as shown below:

ON TITLE PAGE:

Under References Cited U.S. PATENT DOCUMENTS
"4,331,872 5/1982 Saga et al. ... 250/310" should read
--4,331,872 5/1982 Soga et al. ... 250/310--.

Column 1 Line 35 "energydispersive" should read --energy-dispersive--.

Column 3 Line 36 "enerqies" should read --energies--.

Column 4 Line 3 after "unit" insert --11--.

Column 4 Line 57 "intO" should read --into--.

Signed and Sealed this

Seventh Day of July, 1992

*Attest:*

DOUGLAS B. COMER

*Attesting Officer*     *Acting Commissioner of Patents and Trademarks*